(12) United States Patent
Hyde et al.

(10) Patent No.: US 8,495,762 B2
(45) Date of Patent: *Jul. 30, 2013

(54) SHAPE CHANGING MATERIAL

(75) Inventors: Roderick A. Hyde, Redmond, WA (US);
Muriel Y. Ishikawa, Hillcrest, CA (US);
Jordin T. Kare, Seattle, WA (US);
Lowell L. Wood, Jr., Bellevue, WA (US)

(73) Assignee: The Invention Science Fund I LLC

( * ) Notice: Subject to any disclaimer, the term of this patent is extended or adjusted under 35 U.S.C. 154(b) by 0 days.

This patent is subject to a terminal disclaimer.

(21) Appl. No.: 13/605,601

(22) Filed: Sep. 6, 2012

(65) Prior Publication Data

US 2012/0324616 A1    Dec. 27, 2012

Related U.S. Application Data

(63) Continuation of application No. 12/387,481, filed on Apr. 30, 2009, now Pat. No. 7,992,217, and a continuation of application No. 12/660,517, filed on Feb. 26, 2010, and a continuation of application No. 13/135,445, filed on Jul. 5, 2011, now Pat. No. 8,272,069.

(51) Int. Cl.
*G05B 19/21* (2006.01)
*G05B 19/39* (2006.01)
*A63B 26/00* (2006.01)

(52) U.S. Cl.
USPC .................. 2/1; 2/905; 700/66; 482/1; 482/5; 482/9; 482/92; 482/148

(58) Field of Classification Search
USPC ................ 2/1, 905; 700/56–66, 69; 482/1, 482/5, 8, 9, 92, 148; 600/587, 595
See application file for complete search history.

(56) References Cited

U.S. PATENT DOCUMENTS

| | | | |
|---|---|---|---|
| 4,007,733 A | 2/1977 | Celeste et al. | |
| 5,283,735 A * | 2/1994 | Gross et al. | 600/587 |
| 5,749,365 A | 5/1998 | Magill | |
| 6,119,516 A | 9/2000 | Hock | |
| 6,127,672 A * | 10/2000 | Danisch | 250/227.14 |
| 6,360,615 B1 | 3/2002 | Smela | |
| 6,527,711 B1 * | 3/2003 | Stivoric et al. | 600/300 |
| 6,551,252 B2 | 4/2003 | Sackner et al. | |
| 6,563,107 B2 | 5/2003 | Danisch et al. | |
| 6,656,097 B2 | 12/2003 | Karecki | |
| 6,809,462 B2 | 10/2004 | Pelrine et al. | |
| 6,810,300 B1 | 10/2004 | Woltman et al. | |
| 6,913,559 B2 * | 7/2005 | Smith | 482/4 |
| 7,113,848 B2 | 9/2006 | Hanson | |
| 7,138,075 B2 | 11/2006 | Anquetil et al. | |
| 7,160,286 B2 | 1/2007 | Lammer | |
| 7,191,803 B2 | 3/2007 | Orr et al. | |
| 7,303,534 B2 * | 12/2007 | Kahn | 600/587 |
| 7,319,815 B2 | 1/2008 | Seo | |
| 7,337,810 B2 | 3/2008 | Orr et al. | |
| 7,649,975 B2 * | 1/2010 | Boyden et al. | 378/45 |
| 7,653,173 B2 * | 1/2010 | Boyden et al. | 378/44 |

(Continued)

*Primary Examiner* — Bobby Muromoto, Jr.

(57) ABSTRACT

An apparatus is configured with one or more sensors arranged to detect a first shape-related parameter, one or more control elements arranged to provide a force, and circuitry operably connected to the one or more sensors and the one or more control elements to determine the force provided to the one or more control elements.

33 Claims, 8 Drawing Sheets

U.S. PATENT DOCUMENTS

| | | | |
|---|---|---|---|
| 7,660,385 B2 * | 2/2010 | Boyden et al. | 378/44 |
| 7,664,224 B2 * | 2/2010 | Boyden et al. | 378/45 |
| 7,702,066 B2 * | 4/2010 | Boyden et al. | 378/45 |
| 7,724,867 B2 * | 5/2010 | Boyden et al. | 378/44 |
| 7,738,627 B2 * | 6/2010 | Boyden et al. | 378/44 |
| 7,773,722 B2 * | 8/2010 | Boyden et al. | 378/44 |
| 7,825,376 B2 * | 11/2010 | Boyden et al. | 250/305 |
| 7,992,217 B2 * | 8/2011 | Hyde et al. | 2/1 |
| 8,272,069 B2 * | 9/2012 | Hyde et al. | 2/1 |
| 2001/0029224 A1 | 10/2001 | Karecki | |
| 2003/0135127 A1 | 7/2003 | Sackner et al. | |
| 2003/0195623 A1 * | 10/2003 | Marchitto et al. | 623/7 |
| 2004/0007695 A1 | 1/2004 | Anquetil et al. | |
| 2004/0077969 A1 * | 4/2004 | Onda et al. | 600/547 |
| 2004/0133081 A1 * | 7/2004 | Teller et al. | 600/300 |
| 2004/0199232 A1 | 10/2004 | Wallace et al. | |
| 2004/0249510 A1 | 12/2004 | Hanson | |
| 2005/0034485 A1 | 2/2005 | Klefstad-Sillonville et al. | |
| 2005/0054941 A1 | 3/2005 | Ting et al. | |
| 2005/0090767 A1 * | 4/2005 | Kahn | 600/587 |
| 2005/0187527 A1 | 8/2005 | Rix | |
| 2006/0122528 A1 | 6/2006 | Gal | |
| 2006/0122544 A1 | 6/2006 | Ciluffo | |
| 2006/0124193 A1 | 6/2006 | Orr et al. | |
| 2006/0142658 A1 | 6/2006 | Perkuhn et al. | |
| 2006/0192465 A1 | 8/2006 | Kornbluh et al. | |
| 2006/0228970 A1 | 10/2006 | Orr et al. | |
| 2006/0258247 A1 | 11/2006 | Tao et al. | |
| 2006/0264730 A1 * | 11/2006 | Stivoric et al. | 600/390 |
| 2007/0038331 A1 | 2/2007 | Hanson | |
| 2007/0083096 A1 | 4/2007 | Paradiso | |
| 2007/0215839 A1 | 9/2007 | Anquetil et al. | |
| 2007/0265140 A1 * | 11/2007 | Kim et al. | 482/8 |
| 2008/0015454 A1 | 1/2008 | Gal | |
| 2008/0125289 A1 * | 5/2008 | Pryor et al. | 482/8 |
| 2008/0221488 A1 * | 9/2008 | Kurono et al. | 600/595 |
| 2009/0084951 A1 * | 4/2009 | Boyden et al. | 250/307 |
| 2009/0086892 A1 * | 4/2009 | Boyden et al. | 378/44 |
| 2009/0086893 A1 * | 4/2009 | Boyden et al. | 378/44 |
| 2009/0086894 A1 * | 4/2009 | Boyden et al. | 378/44 |
| 2009/0086895 A1 * | 4/2009 | Boyden et al. | 378/44 |
| 2009/0086896 A1 * | 4/2009 | Boyden et al. | 378/44 |
| 2009/0086899 A1 * | 4/2009 | Boyden et al. | 378/45 |
| 2009/0086900 A1 * | 4/2009 | Boyden et al. | 378/45 |
| 2009/0086901 A1 * | 4/2009 | Boyden et al. | 378/45 |
| 2009/0086902 A1 * | 4/2009 | Boyden et al. | 378/45 |
| 2009/0086903 A1 * | 4/2009 | Boyden et al. | 378/45 |
| 2009/0086904 A1 * | 4/2009 | Boyden et al. | 378/45 |
| 2009/0086905 A1 * | 4/2009 | Boyden et al. | 378/46 |
| 2010/0121227 A1 * | 5/2010 | Stirling et al. | 600/595 |
| 2010/0121228 A1 * | 5/2010 | Stirling et al. | 600/595 |
| 2010/0130889 A1 * | 5/2010 | Toth et al. | 600/587 |
| 2010/0280416 A1 * | 11/2010 | Hyde et al. | 600/587 |

* cited by examiner

SHAPE CHANGING MATERIAL

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation of U.S. patent application Ser. No. 12/387,481, entitled SHAPE CHANGING MATERIAL, naming Roderick A. Hyde, Muriel Y. Ishikawa, Jordin T. Kare, Lowell L. Wood, Jr., as inventors, filed 30 Apr. 2009, now U.S. Pat. No. 7,992,217, which is currently co-pending or is an application of which a currently co-pending application is entitled to the benefit of the filing date.

For purposes of the USPTO extra-statutory requirements, the present application constitutes a continuation of U.S. patent application Ser. No. 12/660,517, entitled SHAPE SENSING CLOTHES TO INFORM THE WEARER OF A CONDITION, naming Roderick A. Hyde, Muriel Y. Ishikawa, Jordin T. Kare, Lowell L. Wood, Jr., and Victoria Y. H. Wood, as inventors, filed 26 Feb. 2010, which is currently co-pending or is an application of which a currently co-pending application is entitled to the benefit of the filing date.

For purposes of the USPTO extra-statutory requirements, the present application constitutes a continuation of U.S. patent application Ser. No. 13/135,445, entitled SHAPE CHANGING MATERIAL, naming Roderick A. Hyde, Muriel Y. Ishikawa, Jordin T. Kare, Lowell L. Wood, Jr., and Victoria Y. H. Wood, as inventors, filed 5 Jul. 2011, now U.S. Pat. No. 8,272,069, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

In one embodiment, an apparatus comprises a garment including: a fabric; one or more sensors, the one or more sensors being arranged to detect a first shape-related parameter of the fabric and responsive to the detected first shape-related parameter to produce a first signal; and one or more control elements responsive to a second signal different from the first signal, the one or more control elements being arranged to provide a force on the fabric corresponding to the second signal. The apparatus further comprises circuitry responsive to the first signal to determine a first shape of the fabric and configured to produce the second signal according to a first determined change in the fabric shape.

In another embodiment, an apparatus comprises a fabric having a shape and including: one or more sensors, the one or more sensors being arranged to detect a first shape-related parameter of the fabric and responsive to the detected first shape-related parameter to produce a first signal; and one or more control elements responsive to a second signal different from the first signal, the one or more control elements being arranged to provide a force on the fabric corresponding to the second signal. The apparatus further comprises circuitry responsive to the first signal to determine an adjusted change in the fabric shape and configured to produce the second signal according to the determined adjusted change in the fabric shape.

In another embodiment, a method comprises: receiving a first signal corresponding to a first region of fabric; processing the first signal to produce a first set of fabric shape changing data; producing a second signal based on the first set of fabric shape changing data; and transmitting the second signal corresponding to a second region of fabric.

In another embodiment, a method comprises: sensing a first shape-related parameter, the first shape-related parameter corresponding to a first region of fabric; responsive to the sensed first shape-related parameter, producing a first fabric shape changing signal; and applying force to a second region of fabric according to the first fabric shape changing signal.

In another embodiment, an apparatus comprises: means for receiving a first signal corresponding to a first region of fabric; means for processing the first signal to produce a first set of fabric shape changing data; means for producing a second signal based on the first set of fabric shape changing data; and means for transmitting the second signal corresponding to a second region of fabric.

In another embodiment, a method comprises: producing a first set of initial condition data corresponding to a predicted first shape of a first region of fabric; processing the produced first set of initial condition data to produce a first set of fabric shape changing data for a second region of fabric; and applying force to a second region of fabric according to the first set of fabric shape changing data.

In another embodiment, an apparatus comprises: circuitry configured to receive a first signal corresponding to a first region of fabric; circuitry configured to process the first signal to produce a first set of fabric shape changing data; circuitry configured to produce a second signal based on the first set of fabric shape changing data; and circuitry configured to transmit the second signal corresponding to a second region of fabric.

In another embodiment, an apparatus comprises a garment including: a fabric; and one or more control elements responsive to a second signal different from the first signal, the one or more control elements being arranged to provide a force on the fabric corresponding to the second signal. The apparatus further comprises: one or more sensors, the one or more sensors being arranged to detect a first shape-related parameter of the fabric and responsive to the detected first shape-related parameter to produce a first signal; and circuitry responsive to the first signal to determine a first shape of the fabric and configured to produce the second signal according to a first determined change in the fabric shape.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
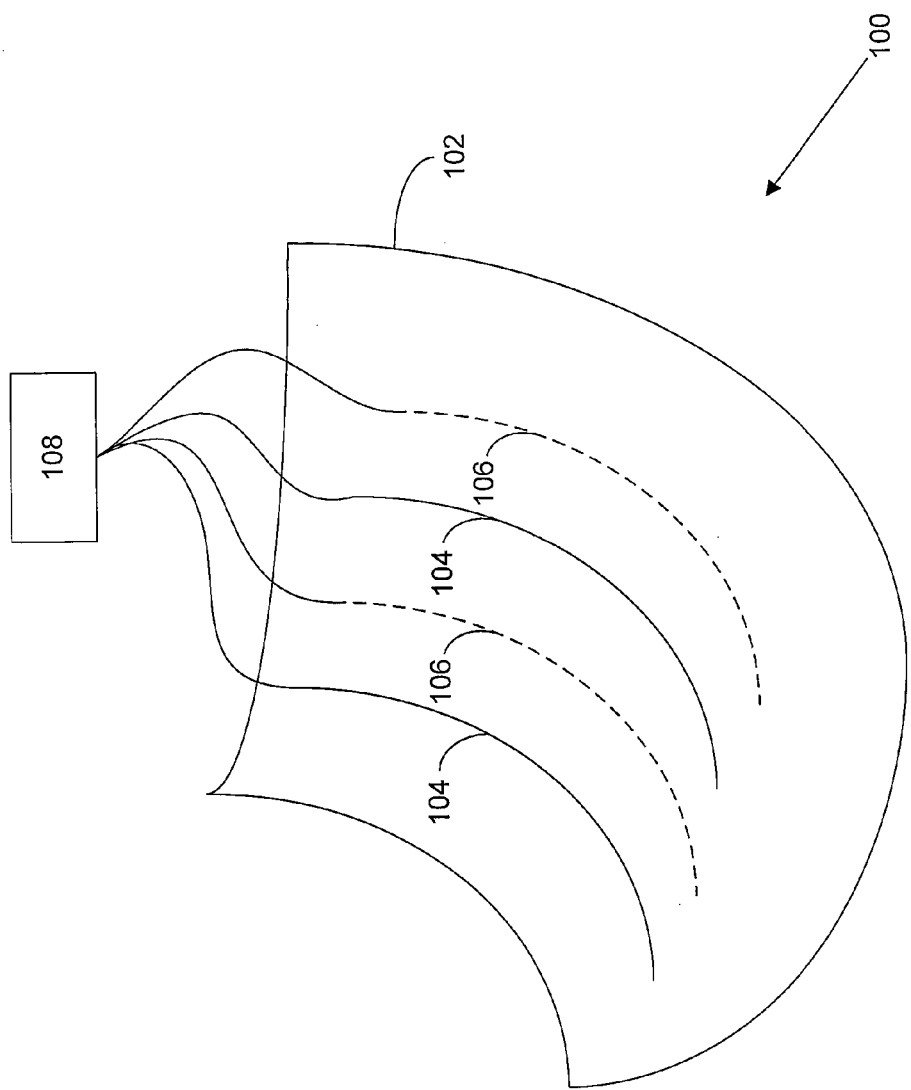
FIG. 1 shows an apparatus including a fabric and circuitry.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 2:
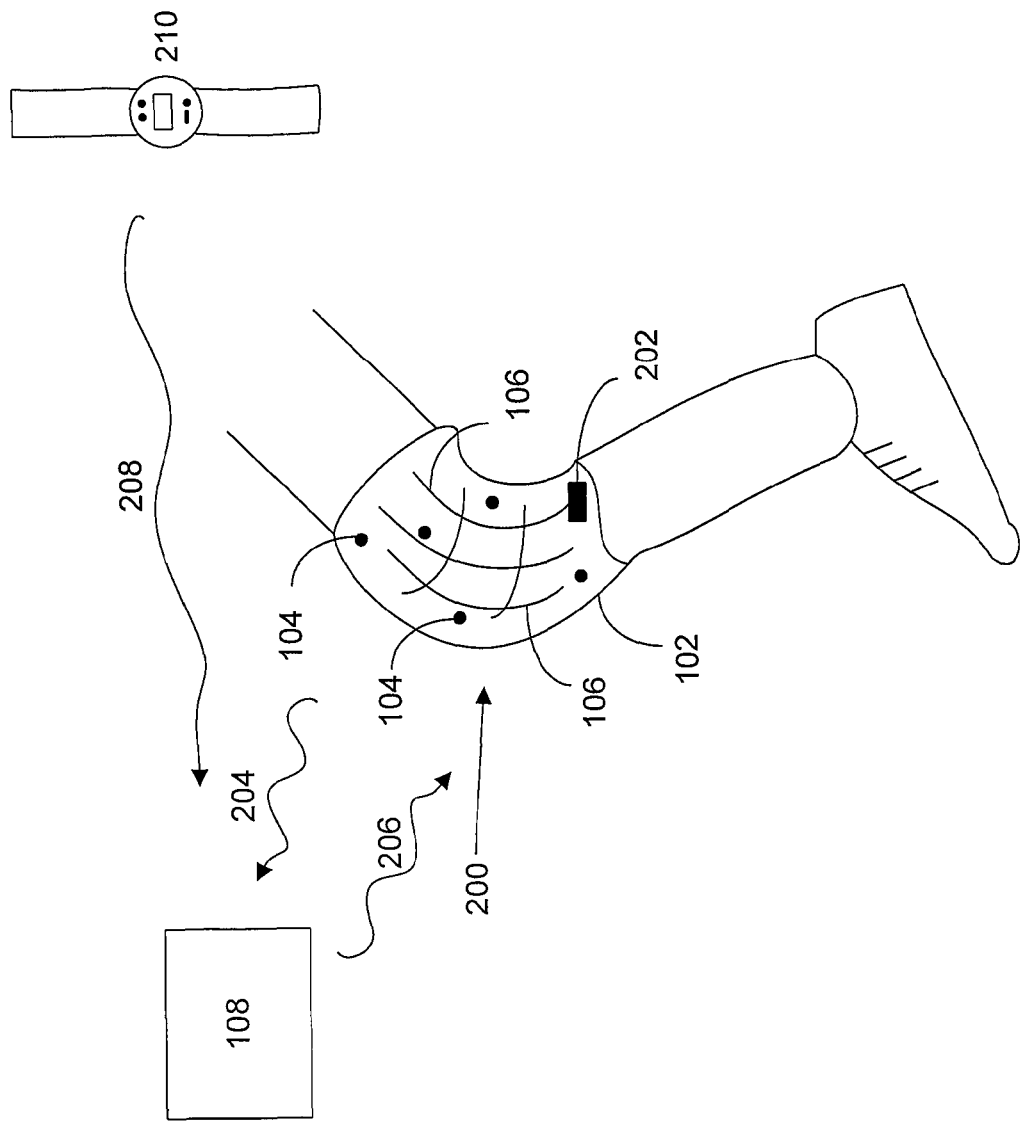
FIG. 2 shows an apparatus including a garment, circuitry, and a user input.

In one embodiment, depicted in FIG. 1, an apparatus 100 comprises a fabric 102, one or more sensors 104 arranged to detect a first shape-related parameter of the fabric 102 and responsive to the detected first shape-related parameter to produce a first signal; and one or more control elements 106 responsive to a second signal different from the first signal, the one or more control elements 106 being arranged to provide a force on the fabric 102 corresponding to the second signal. The apparatus 100 further comprises circuitry 108 responsive to the first signal to determine a first shape of the fabric 102 and configured to produce the second signal according to a first determined change in the fabric shape. FIG. 2 shows the fabric 102 forming a portion of a garment 200, where the garment 200 shown in FIG. 2 is a knee brace.

The first shape-related parameter may include a variety of different parameters depending on what the fabric 102 is incorporated into. For example, where the fabric 102 forms at least part of a garment, the first shape-related parameter may be a force due to motion of the user, impact with something, stress/strain on the fabric due to stretching, or a different parameter. Where the fabric forms at least part of a sail, the first shape-related parameter may be a force due to wind relative to the motion of the sail. Where the fabric forms at least part of a racket, the first shape-related parameter may be a force due to a collision between the fabric and a target, such as a ball. The first shape-related parameter may include a force, a stress, a pressure, a strain, a bend, a twist, a deformation, a geometry, a surface topology, an orientation, a reflection, or a position of one or more portions of the fabric 102.

There are many different applications for the fabric 102 and one skilled in the art may incorporate the fabric 102 into a different device. The one or more sensors 104 may sense strain, bends, or twists, or a different type of force, and may include, for example, optical fibers and/or conductive fibers that provide a change in electrical conductivity according to their contact with a body, as will be described in more detail in the following.

The fabric 102 may include a number of materials, including but not limited to metal, polyester, Tyvek®, nylon, spandex, rayon, cotton, wool, leather, linen, soy, bamboo, rubber, down, silk, paper, a blend of materials, or a material not listed here. The fabric 102 may include an organic material, an inorganic material, or a combination of both. The fabric 102 may be a woven fabric or a non-woven fabric. In some embodiments the fabric 102 may include a recycled material, wherein the recycled material may derive from paper, from a synthetic material, or from a different source. In some embodiments the fabric 102 may be configured to produce a relatively tight fit, and in this case appropriate materials such as spandex or a different elastic material may be selected.

Although FIG. 1 portrays the one or more sensors 104 as isolated sensors on the fabric 102, in other embodiments the one or more sensors 104 may have a different configuration. For example, the one or more sensors 104 may include, for example, conductive fibers woven throughout the fabric 102.

The one or more sensors 104 and/or the one or more control elements 106 may be operably connected to the circuitry 108 and/or one or more other components, such as a power source 402 (shown in FIG. 4) and/or a detector. The connection may be electrical, electromagnetic, ultrasonic, acoustic, or via a different kind of connection. Examples of electromagnetic energy may include a photonic signal, a wireless electromagnetic signal, and/or a different kind of signal including electromagnetic energy, and may incorporate wavelengths the optical and/or RF portion of the electromagnetic spectrum, other portions of the electromagnetic spectrum, or a variety of different spectral bands. The electromagnetic signal may be guided, such as via an optical fiber or other type of guide, unguided, such as in wireless transmission, or some combination of both. The connection may be a type of connection not listed here, such as a mechanical and/or pneumatic connection, and one skilled in the art may apply established communication techniques according to the particular embodiment.

Depending on the type of connection the apparatus may further include one or more converters 202, as shown in FIG. 2, arranged to convert one type of energy into another type of energy (for example, electrical energy to electromagnetic energy or electromagnetic energy to electrical energy). In some embodiments, first and second signals may be sent and/or received wirelessly to the circuitry 108 in a location remote relative to the apparatus 100. In other embodiments the circuitry 108 may be in several locations, such as in the case where minimal processing is done at the location of the fabric 102 and where signals are sent and received to/from a remote location for other processing. Such a setup would allow for miniaturization of the processor such that it may be incorporated in the fabric, but also allow for processing done by a larger processor by wirelessly communicating with said processor. There are many different permutations of the different technologies presented herein and one skilled in the art may combine the different technologies according to a specific application.

The one or more sensors 104 may include one or more of a variety of technologies arranged to detect a force on the fabric 102. For example, the one or more sensors 104 may include one or more transducers (which may include an electroactive polymer) that produce an electrical change with mechanical deflection or mechanical strain (such as a stretch in the fabric 102). One example of such a sensor is described in U.S. Pat. No. 6,809,462 to Pelrine et al., entitled ELECTROACTIVE POLYMER SENSORS, which is incorporated herein by reference.

In another embodiment the one or more sensors 104 may be configured to measure bend and/or twist, and may include optical fibers and/or electrically conductive fibers, examples of which are described in U.S. Pat. No. 6,127,672 to Danisch et al., entitled TOPOLOGICAL AND MOTION MEASURING TOOL, and in U.S. Pat. No. 6,563,107 to Danisch et al., entitled TOPOLOGICAL AND MOTION MEASURING TOOL, each of which is incorporated herein by reference.

In another embodiment the one or more sensors 104 may be configured to detect strain, pressure, and/or position by detecting changes in electrical impedance in conductive fibers, an example of which is described in U.S. Pat. App. No. 2006/0258247 to Tao et al., entitled PRESSURE SENSING FABRIC, which is incorporated herein by reference. Other examples of detecting changes in electrical impedance to determine strain are described in U.S. Pat. No. 6,360,615 to Smela, entitled WEARABLE EFFECT-EMITTING STRAIN GAUGE DEVICE, and in U.S. Pat. App. No. 2004/0199232 to Wallace et al., entitled FEEDBACK DEVICE HAVING ELECTRICALLY CONDUCTIVE FABRIC, each of which is incorporated herein by reference.

The one or more sensors 104 may include other types of sensors, such as a camera, a shape sensor, a position sensor, a separation sensor configured to measure the separation between two points, or a different type of sensor. The one or more sensors 104 may also include one or more components and/or devices which operate in conjunction with the sensor to measure the shape-related property of the fabric, including but not limited a reflector, a retroreflector, a beacon (where the beacon may be configured to use: electromagnetic energy, including but not limited to optical energy, RF energy, or a different band of electromagnetic energy; ultrasonic energy; or a different kind of energy), an RFID, or a different type of marker, target, and/or other device.

The one or more sensors 104 may further be configured to provide a location, magnitude, and/or direction of a detected force, a detected stress, or a detected strain.

The one or more control elements 106 may include one or more of a variety of technologies arranged to provide a force on the fabric 102. For example, in one embodiment the one or more control elements 106 may include an electroactive polymer, as described in U.S. Pat. No. 7,138,075, U.S. Pat. App. No. 2004/0007695, and U.S. Pat. App. No. U.S. 2007/0215839, each of which is to Anquetil et al., each of which is entitled MOLECULAR ACTUATORS, AND METHODS OF USE THEREOF, and each of which is incorporated herein by reference. Further description of the use of electroactive polymers as a control element is described in U.S. Pat. App. No. 2007/0265140 to Kim et al., entitled APPARATUS AND METHOD ENHANCING MUSCULAR MOVEMENT, which is incorporated herein by reference.

In other embodiments the one or more control elements 106 may include an array of mechanical actuators, one example of which is described in U.S. Pat. No. 7,113,848, U.S. Pat. App. No. 2004/0249510, and U.S. Pat. App. No. 2007/0038331, each of which is to Hanson et al., each of which is entitled HUMAN EMULATION ROBOT SYSTEM, and each of which is incorporated herein by reference.

In other embodiments the one or more control elements 106 may include a mechanical metamaterial, one example of which is described in U.S. Pat. App. No. 2006/0192465 to Kornbluh et al., entitled MECHANICAL META-MATERIALS, which is incorporated herein by reference.

Other embodiments may include one or more control elements 106 not listed above, such as: hydraulic, pneumatic, electrical, magnetic, thermally induced, and/or chemoactive control elements, MEMS, or mechanical elements such as levers, pulleys, or a different type of control element not listed here. The choice of the one or more control elements 106 may depend on a number of factors, such as the size and/or scale of the fabric 102, the type of fabric 102, the variations in dimensions of the fabric 102, and/or other factors.

The one or more control elements 106 may be dynamically variable in some embodiments such that they may vary continuously, in response to the motion of the user or in response to a different stimulus. The one or more control elements 106 may further be configured to provide a magnetic force, a thermally induced force, or a different kind of force on the fabric 102. Further, the one or more control elements 106 may be configured to provide a force on one or more individual fibers in the fabric 102, where the force may include a longitudinal stretching force, a lateral force, a bending moment, a bending force, or a torque. The one or more control elements 106 may be external to the fabric 102, proximate to the fabric 102, integral to the fabric 102, or have some other positioning relative to the fabric 102. The one or more control elements 102 may be configured to provide a force transversely to the fabric 102 or in a different direction relative to the fabric 102.

In the case where the one or more sensors 104 and/or the one or more control elements 106 include two or more sensors 104 and/or control elements 106, they may be configured in an array, which may be regular or irregular. Further, the one or more sensors 104 may be configured to provide one or more corresponding measurements, the one or more corresponding measurements being associated with one or more corresponding regions of the fabric, such as in the case where the one or more sensors 104 includes a camera, and the camera obtains information related to an array of regions corresponding to the fabric 102. Such regions may form a regular array or an irregular array. In this embodiment, the one or more corresponding measurements may at least partially determine the detected first shape-related parameter.

The fabric 102 may be included in a variety of different applications. For example, the fabric 102 may form all or part of a garment, such as a knee brace, which will be described in greater detail with respect to FIG. 2. In embodiments including garments the one or more sensors 104 may be located at or proximate to a joint or other location where twist or bend may occur, such as a knee, elbow, knuckle, or waist, however these are just examples of where the one or more sensors 104 may be located and the location of the one or more sensors 104 may depend on the particular embodiment. In one embodiment, a garment may be designed for those with circulatory problems, such as support hose or other garments. In such an embodiment, the circuitry 108 may also receive input from an outside source such as a heart rate monitor, thermometer, or other source (for example, the input 210 as shown in FIG. 2), where the circuitry 108 may be further responsive to a signal from the outside source to determine the adjusted change in fabric shape.

In another embodiment the fabric 102 may be incorporated into shapewear, where the garment includes one or more sensors 104 for determining an unmodulated shape of the person and one or more control elements 106 for adjusting the shape of the garment to produce a modulated shape of the person. For example, the one or more sensors 104 may be configured to detect stress and/or strain on the garment, and the one or more control elements 106 may be configured to alter the shape of the garment until the stress and/or strain on the one or more sensors 104 goes above or below a certain threshold value.

In another embodiment the fabric 102 may be incorporated into self-fitting garments that are initially quite loose and, when put on a body, detect the shape of the body and self-fit accordingly. Such clothing may be useful, for example, for elderly or injured people, those people who may have difficulty with small buttons and snaps, etc. In another embodiment the fabric 102 may be incorporated in a device targeted for therapeutic uses such as a bandage designed to reduce swelling. In this embodiment the sensors may be configured to detect swelling according to stresses on the fabric 102 and may apply compression to those areas where swelling is detected, where the location and amount of compression is related to the location and amount of swelling.

FIG. 2 shows an embodiment in which the fabric 102 is incorporated into a garment 200, where in this embodiment the garment 200 is a knee brace. In the embodiment of FIG. 2 the one or more control elements 106 include a shape memory material which expands and contracts depending on a voltage applied to the material, causing the fabric 102 to expand and contract accordingly and causing the garment 200 to tighten and loosen correspondingly. In this embodiment the one or more sensors 104 and the one or more control elements 106 are operably connected to a converter 202 that is configured to communicate wirelessly with the circuitry 108. Thus the converter 202 in this embodiment is configured to convert an electrical signal to an electromagnetic signal, and to convert an electromagnetic signal to an electrical signal. FIG. 2 symbolically shows the first signal 204 produced by the one or more sensors 104 and the second signal 206 to which the one or more control elements 106 are responsive.

FIG. 2 further shows a user input 210. In the embodiment shown in FIG. 2 the user input 210 is a device that may be worn on the user's wrist and is configured to communicate wirelessly to produce the signal 208 (shown symbolically) to communicate with the circuitry 108. However, in different embodiments the user input 210 may have a different form, such as a switch located on the garment 200 such that the user may select different settings, or the user input 210 may be located proximate to the circuitry 108. There are many different forms that a user input 210 may take and many different ways that it may be incorporated with a garment 200, and the example of a device the user wears on the wrist is just one of many different forms that the user input 210 may take.

In the embodiment shown in FIG. 2 the user input 210 is such that the user can select from a variety of settings. The settings may allow the user to select initial conditions around which the circuitry 108 may adjust. However, in other embodiments the user input 210 may be directly connected to the circuitry 108. For example, in some embodiments the circuitry 108 may provide the user with options for adjustments to be made to the fabric, where the user may select from the options. In some embodiments the user may select from a range of possible shapes and/or sizes of a garment. Or, the user may input data into the system to be included in the data processing, such as one or more measurements, uses for the garment, temperature, or a different piece of information.

There are many different ways that user input 210 may be incorporated in such a device and one skilled in the art can tailor the user input 210 according to a particular embodiment. FIG. 2 shows the user input 210 producing the third signal 208. However, in other embodiments the circuitry 108 may be responsive to a third signal 208, where the third signal 208 is not produced by a user input 210. For example, a thermometer configured to measure ambient temperature may be configured to produce the third signal 208. Or, another device may be configured to measure a physiological parameter of the user, such as heart rate and/or body temperature, and produce the third signal 208 accordingly. There are many different configurations for which input of the third signal 208 to the circuitry may be useful.

Although FIG. 2 shows the circuitry 108 as being separate from the user input 210 and from the garment 200, in other embodiments the circuitry may be in a different location. The circuitry 108 may be located, for example, in a device such as that housing the user input 210 that the user may wear on their wrist, it may be part of a treadmill or other exercise device, or it may be in a different location. The circuitry 108 may be geographically separate from the garment 200. There are many different locations where it may be advantageous to have the circuitry 108, and different embodiments may include different remote locations of the circuitry 108. Further, although the circuitry 108 is shown as being separate from the fabric 102 in the embodiment of FIG. 2, in other embodiments the circuitry 108 may be on or integral to the fabric 102.

Although FIG. 2 shows only a few of the one or more sensors 104 and the one or more control elements 106 for illustrative purposes, the number, locations, and/or density of the one or more sensors 104 and the one or more control elements 106 may be different from that portrayed in FIG. 2. For example, the fabric 102 may include thousands of sensors 104 and/or control elements 106 woven together. Further, although FIG. 2 shows the one or more sensors 104 and one or more control elements 106 as being substantially separate from the fabric 102 for illustrative purposes, in other embodiments the one or more sensors 104 and/or the one or more control elements 106 may form part or even all of the fabric 102. In different embodiments the fabric 102 may includes sensors 104 and/or control elements 106 in regularly-spaced intervals, or in random and/or irregularly spaced intervals, depending on the application and/or method of fabrication.

The one or more sensors 104 may be configured to sense a variety of different things. For example, the one or more sensors 104 may be configured to determine the shape of the fabric 102 and/or the shape of a body part proximate to the fabric 102, where in this case the body part is a knee. Such an embodiment may be employed in an embodiment, for example, where the garment 200 is used to provide measurements of a person, for medical and/or therapeutic reasons, for retail purposes such as when the user orders items from a catalog and precise measurements are needed, or for another reason.

Figure 3:
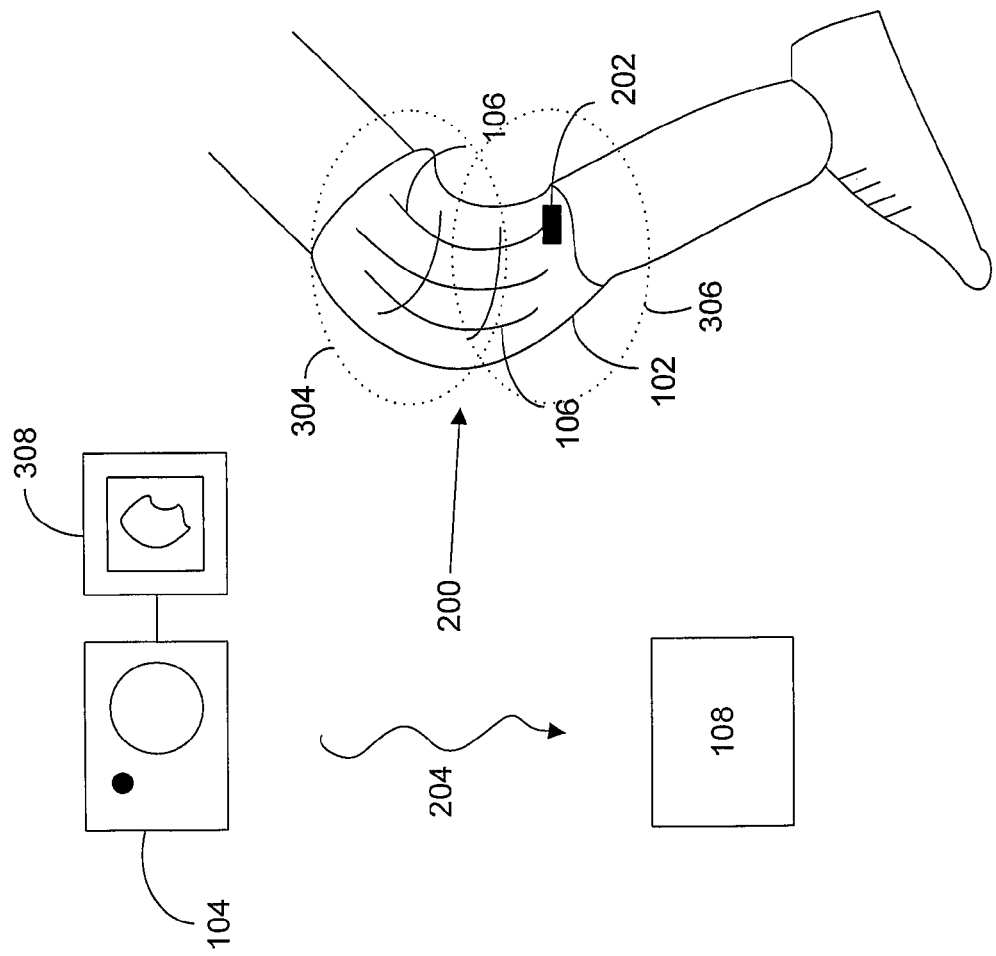
FIG. 3 shows an apparatus including a garment and circuitry.

FIG. 3 shows a garment similar to that of FIG. 2, wherein the one or more sensors 104 includes a camera, wherein the camera is configured to monitor the garment 200 and provide the first signal 204 accordingly to the circuitry 108. Although FIG. 3 shows only a camera as the one or more sensors 104 in FIG. 3, in other embodiments the camera may be employed with other types of sensors. Further, other embodiments may include one or more other or different types of sensors that are external to the garment 200. In some embodiments the camera (the one or more sensors 104 shown in FIG. 3) may be configured to monitor something different from the garment 200, such as user behavior, posture, or a different variable, such that second signal 206 sent to the one or more control elements 106 may be configured according to information regarding such user behavior, posture, etc. Further, although a camera is shown in FIG. 3 as the one or more sensors 104, in some embodiments the one or more sensors 104 may include a different monitoring device, including but not limited to a biological sensor or other device. In this case, the one or more control elements 106 may be configured to stimulate the muscles of the wearer, to provide heat to the wearer, or provide a different therapeutic or other function.

FIG. 3 further includes a display 308 configured to show information received by the one or more sensors 104. Although in FIG. 3 the display is shown as being directly connected to the one or more sensors 104, in other embodiments the display 308 may be operably connected to the circuitry 108, wherein the display may be configured to show processed or unprocessed signals and/or information. Further, FIG. 3 shows the display 308 as showing the entire garment 200, however in other embodiments the display 308 may be configured to show only a portion of the garment 200, and/or may be configured to display the information in a different way than an image. The embodiment may further include a user input, not shown, configured such that a user may select the information received by the one or more sensors 104, where the user may use the display 308 to help guide their selection. In this case the user may be the individual wearing the garment or a different person or thing.

In the embodiment shown in FIG. 3, the garment 200 includes a first region 304 and a second region 306, wherein the garment 200 is configured with one or more control elements 106 such that they provide a force between the first region 304 and the second region 306. Although the first region 304 and the second region 306 are shown as partially overlapping, in other embodiments they may overlap more or less than is shown in FIG. 3, or not at all. Further, the first region 304 and the second region 306 may be on different layers of fabric 102, or may be in a configuration different from that shown in FIG. 3. Further, although the first and second regions 304, 306 are described with respect to FIG. 3 such that the one or more control elements 106 provide a force between the first and second regions 304, 306, in other embodiments the first and second regions may be related in a different way, and the sketching of the different regions 304, 306 is intended for illustrative purposes.

Figure 4:
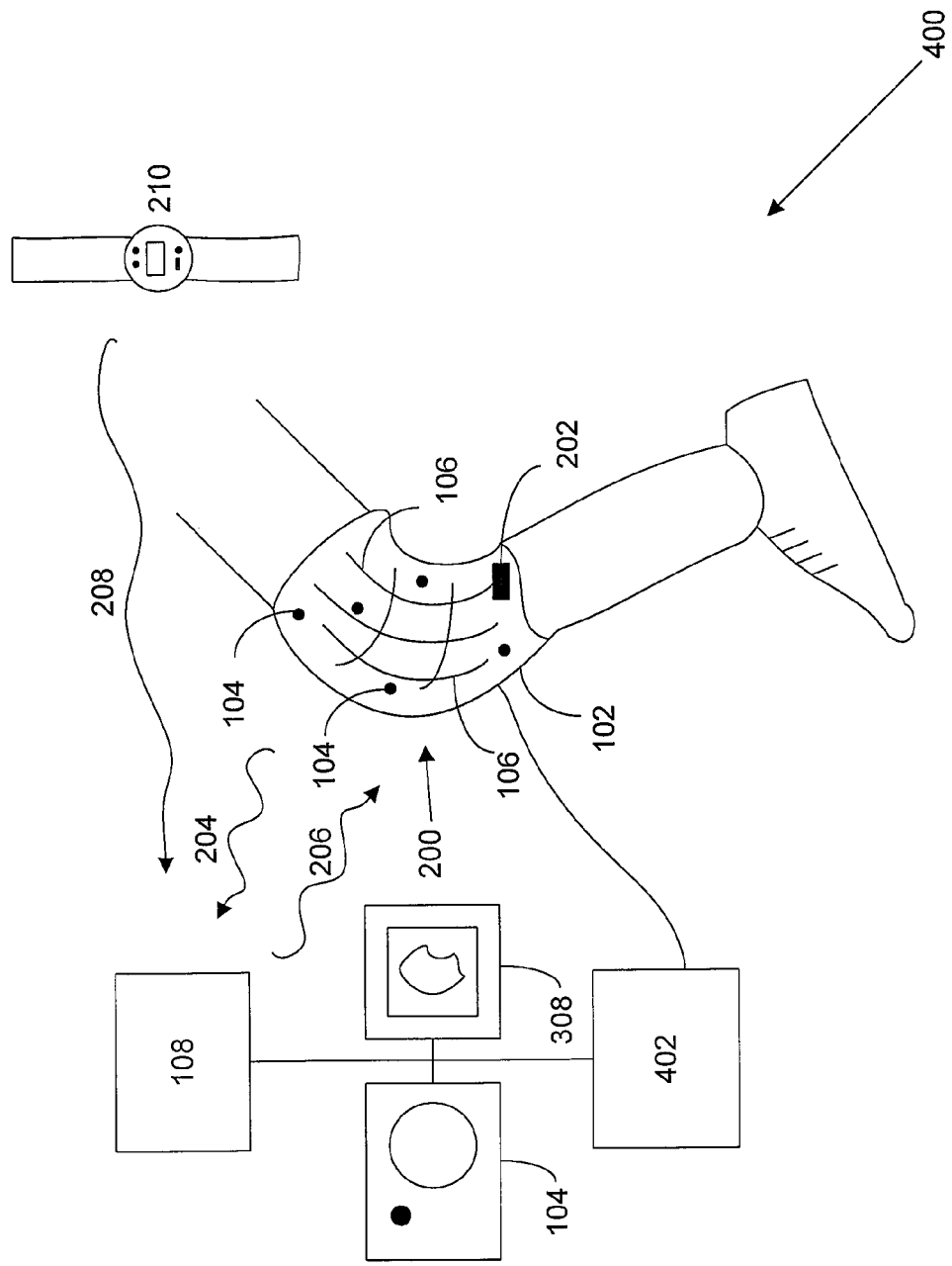
FIG. 4 shows a system including a garment, circuitry, a power source, and a detector.

FIG. 4 shows the garment 200 as part of a system 400. In this embodiment the system 400 includes a power source 402 operably connected to the one or more sensors 104, the one or more control elements 106, the circuitry 108, and the display 308. In other embodiments the power source 402 may be operably connected to provide power to a different combination of components of the system, for example, more components or less components or simply a different combination of components. A power source may be employed to provide power to any number of electronic instruments and/or circuitry that may be implemented in a system such as the system 400 shown in FIG. 4. Further, the system 400 may be configured in a number of different ways, and the system shown in FIG. 4 is just one exemplary embodiment. For example, in some embodiments the circuitry 108 and the display 308 may be housed in the same component. The one or more sensors 104 shown in FIG. 4 include a camera and one or more sensors 104 located on the garment 200, however in other embodiments the system may include a different number or combination of sensors 104. The signals 204, 206, 208 are shown symbolically as waves, indicating electromagnetic, ultrasonic, or a different wave, however the signals 204, 206, 208 may take a different form, such as an electrical signal or other type of signal. Further, several of the components of the system 400 are shown substantially separate from the garment 200, however in some embodiments these components may be located on, in, or proximate to the garment 200. In other embodiments the components may be located substantially separately from the garment 200, such as the case where the one or more sensors 104 include one or more cameras located in a fixed location in a building, for example. There are many different ways that the system of FIG. 4 may be configured and one skilled in the art may tailor the number, type, and configuration of the components according to a particular embodiment.

The circuitry 108 may be configured in a number of different ways. For example, the circuitry 108 may be configured to utilize a computational model to predict the first change in the fabric shape corresponding to the second signal.

Figure 5:
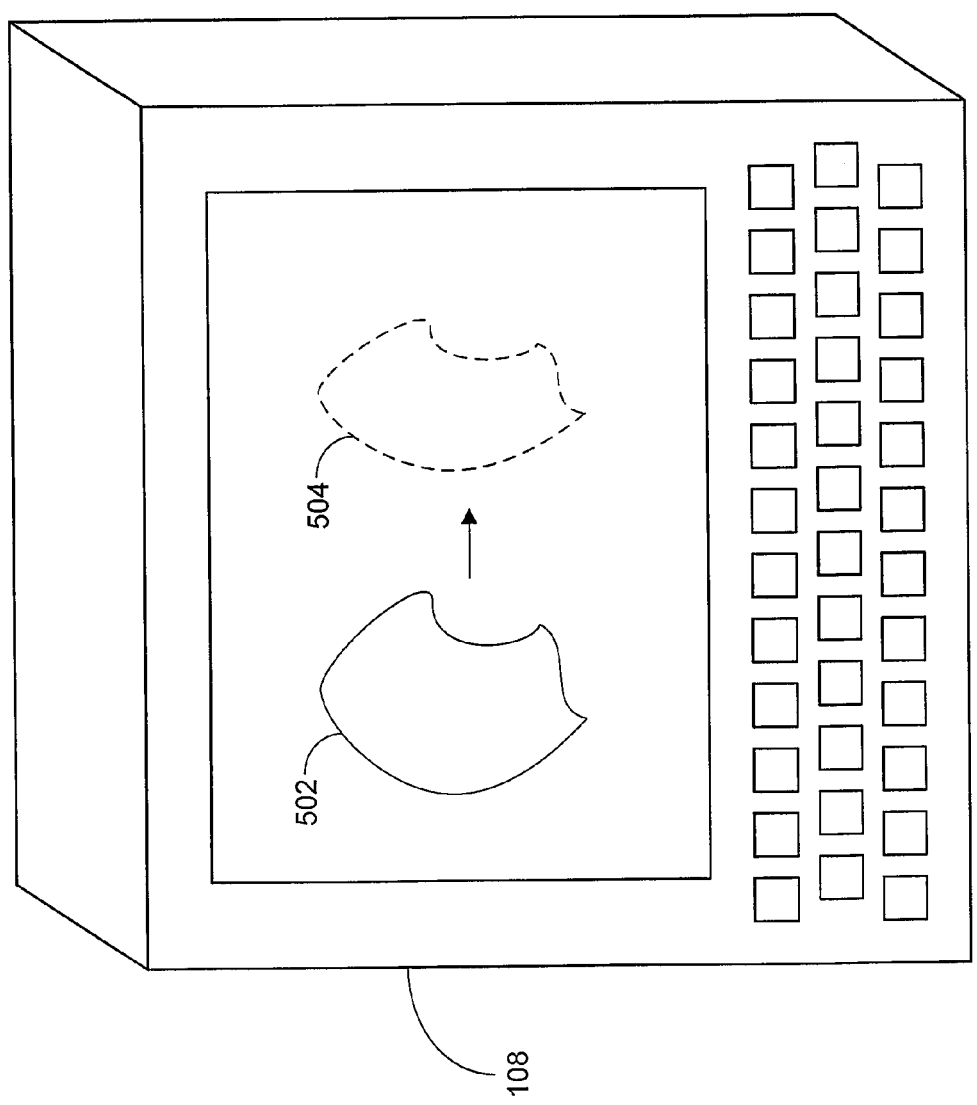
FIG. 5 shows circuitry with a display.

In some embodiments the circuitry may be configured, as shown in FIG. 5, to compare the first shape of the fabric 502 to a first target shape 504, and to determine the first change in the fabric shape according to a difference between the first shape of the fabric 502 and the first target shape 504. The circuitry may be configured to do this iteratively with successive target shapes where each of the successive target shapes may correspond to different times, such as the case where a garment 200 takes a pre-set amount of time to arrive at each target shape.

In some embodiments the circuitry may be configured to determine the first change in the fabric shape according to a rate of change from the first shape of the fabric to the first target shape, wherein the rate of change may correspond to a user-specified rate of change, to a property of the fabric, or to a different value. The circuitry may further be configured to determine the first change in the fabric shape according to a fabric property, wherein the fabric property may include fiber type, fiber dynamics, weave, mass, thickness, density, or a reflective property of the fabric. The circuitry may further be configured to determine the first change in the fabric shape according to a change in a reflective property of the fabric.

In some embodiments the circuitry 108 may include mechanisms for storage of information, and may include one or more histories of detected shape-related parameters, first shape(s) of the fabric, determined change(s) in fabric shape, and/or other values. The circuitry 108 may be configured to determine averages of detected shape-related parameters over time intervals, where the time interval may be selected by a user, pre-determined, or chosen in a different way. Or, the circuitry 108 may be configured to process stored values in other ways. The circuitry 108 may further be configured to compare measurements made in real-time, such as the first shape-related parameter, to similar stored measurements. In some embodiments the determined change in the fabric shape may be based on a difference between a measured parameter and a stored parameter. An example of an embodiment in which stored parameters may be used by the circuitry 108 to determine the first change in the fabric shape includes comparing the measured shape of a body part, such as a joint, leg, or other part of a body, to a previously-measured shape and/or an average of previously-measured shapes to determine swelling, damage, weight loss or gain, or another change in shape, and determining the first change in the fabric shape accordingly. There are many different types of values, measurements, signals, and/or other parameters that may be stored relative to a system such as is represented in FIGS. 1-8 and storage of parameters may be decided according to a particular embodiment. Further, although the storage is described here as being a part of the circuitry 108, in other embodiments the storage may be separate or separable from the circuitry 108.

In one embodiment, an apparatus comprises: means for receiving a first signal corresponding to a first region of fabric; means for processing the first signal to produce a first set of fabric shape changing data; means for producing a second signal based on the first set of fabric shape changing data; and means for transmitting the second signal corresponding to a second region of fabric. These means correspond substantially to the circuitry 108 described with respect to FIGS. 1-8 and with corresponding apparatus as described herein.

Figure 6:
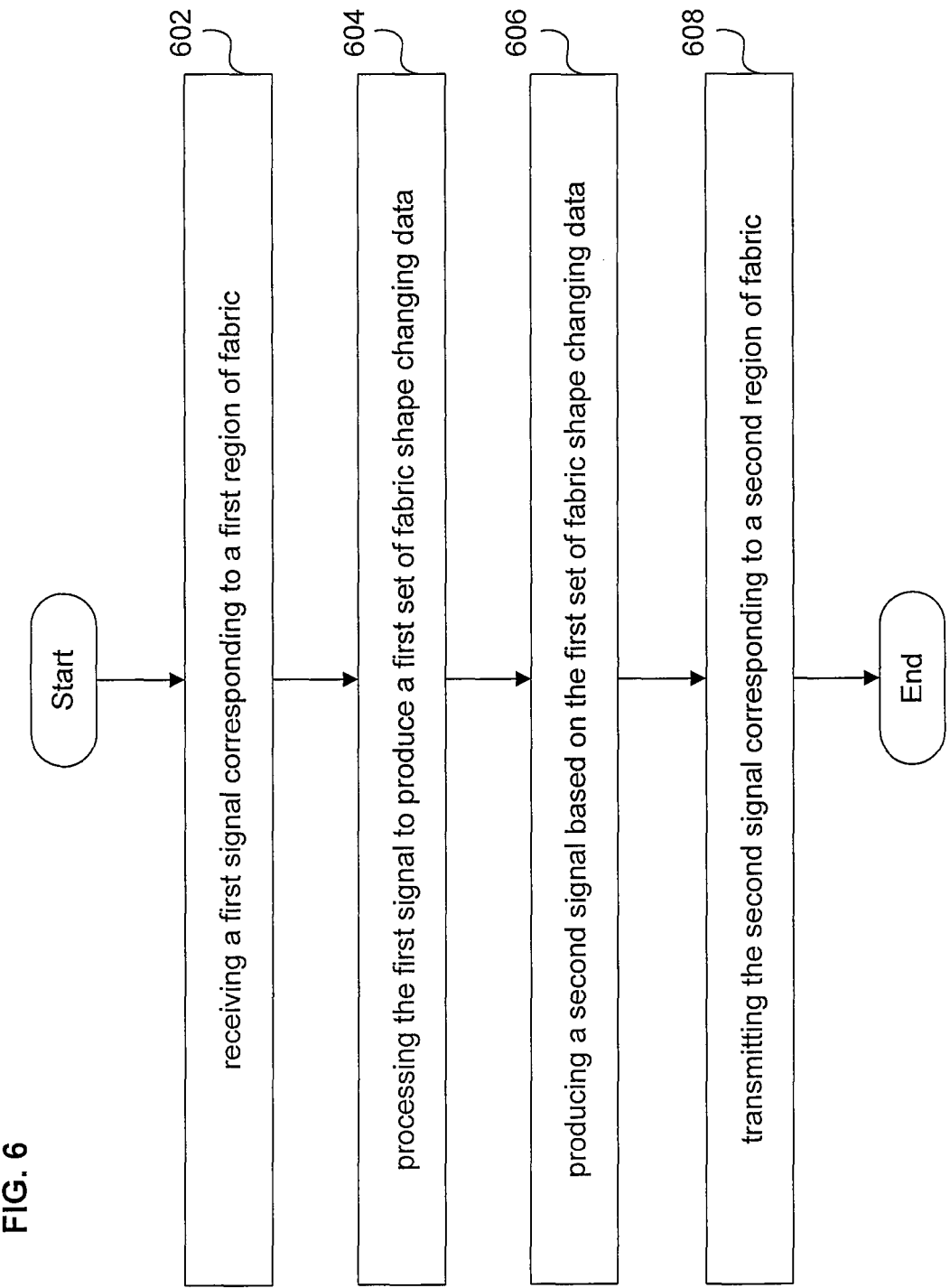
FIG. 6 shows a flow chart depicting a method.

In one embodiment, depicted in the Flow Chart of FIG. 6, a method comprises: (602) receiving a first signal (204) corresponding to a first region of fabric; (604) processing (108) the first signal to produce a first set of fabric shape changing data; (606) producing a second signal (206) based on the first set of fabric shape changing data; and (608) transmitting the second signal to a second region of fabric.

In this embodiment, the first region of fabric may correspond substantially to the second region of fabric, the first region of fabric may partially overlap the second region of fabric, and/or the first region of fabric may be entirely different from the second region of fabric.

The method corresponding to the Flow Chart of FIG. 6 may be understood with respect to FIGS. 1-5, where the first and second regions of fabric may correspond to one or more portions of a garment, such as the garment 200 shown in FIG. 2. Regions of fabric 304, 306 are illustrated in FIG. 3, where in the embodiment of FIG. 3 the regions 304, 306 are partially overlapping. However, in some embodiments the regions 304, 306 may be substantially the same region such that they are almost entirely overlapping. In other embodiments the first and second regions 304, 306 may not be overlapping at all, depending on the particular application.

The method of FIG. 6 may further comprise transmitting the second signal to a third region (not shown) different from the second region of fabric 306 and proximate to the second region of fabric 306, wherein the third region is configured to exert a force on the second region of fabric 306. For example, the garment 200 may include an underlying layer of fabric including the one or more control elements 106, wherein this underlying layer of fabric may include the third region and may be configured to exert a force on the first and/or second regions of fabric 304, 306.

In this embodiment, processing the first signal to produce a first set of fabric shape changing data may include determining a shape of a body part proximate to the first region of fabric 304. For example, with respect to FIG. 2, the one or more sensors 104 may be configured to receive information related to the shape of the knee under the knee brace (the knee brace is the garment 200), and the circuitry 108 may be configured to determine the shape of the knee according to the information received by the one or more sensors 104. The embodiment may further include determining a shape corresponding to the first region of fabric and comparing the body part shape to the first region of fabric shape. In this embodiment, for example, the one or more sensors 104 may include sensors configured to determine the shape of the knee, and sensors configured to determine the shape of the knee brace (the garment 200). This is just one example of a configuration in which different types of sensors may be employed, and other embodiments may include configurations with different types of sensors.

In some embodiments, processing the first signal to produce a first set of fabric shape changing data may include comparing the first signal to a reference signal. For example, with reference to FIG. 2, the first signal may be the signal 204, and the reference signal may be a signal generated by the circuitry 208 and corresponding to, for example, a reference state of the garment 200. The reference signal may correspond to a particular shape of the garment 200, it may correspond to a user specified shape of the garment 200, where the user may produce the reference signal by selecting a particular shape of the garment 200, or the reference signal may be a different kind of reference.

The method of FIG. 6 may further comprise receiving a third signal (208), and processing the third signal 208 to produce the first set of fabric shape changing data. As described previously with respect to FIG. 2, the third signal 208 may include a variety of different information, including but not limited to physiological data such as temperature and/or heart rate, information selected by a user, or a different type of information.

In some embodiments, the first signal 204 and the third signal 208 may both correspond to information related to the fabric 102. For example, the first signal 204 may correspond to the first region of fabric and the third signal 208 may correspond to a third region different from the first region of fabric. Or, the first and third signals 204, 208 may both correspond to the first region of fabric, but the different signals may correspond to different times.

In some embodiments, processing the first signal to produce a first set of fabric shape changing data may further include using a computational model to produce the first set of fabric shape changing data.

In some embodiments, processing the first signal to produce a first set of fabric shape changing data may further include determining a first shape of the first region of fabric (such as the shape 502 shown in FIG. 5) based on the received first signal, which may further include determining an adjusted shape of the first region of fabric (such as the shape 504 shown in FIG. 5) to produce the first set of fabric shape changing data and/or producing the first set of fabric shape changing data based on a difference between the determined first shape (502) of the first region of fabric and a first target shape (such as the shape 504 shown in FIG. 5) of the first region of fabric. In some embodiments the determined first shape 502 may correspond to a first time and the first target shape 504 may correspond to a second time different from the first time, and the first set of fabric shape changing data may further be based on the difference between the first time and the second time. In some embodiments the processes outlined herein may be iterative and/or cumulative including successive target shapes and corresponding signals and processing associated.

In some embodiments, processing the first signal to produce a first set of fabric shape changing data may include processing the first signal according to a fabric property, wherein the fabric property includes at least one of fiber type, fiber dynamics, weave mass, thickness, density, or a reflective property of the fabric. The fabric property may be prior knowledge and part of the circuitry 108, the fabric property may be something that is measured by the one or more sensors 104, the fabric property may be something input by the user input 210, or the fabric property may be obtained and/or used by the circuitry in a different way.

In some embodiments, transmitting the second signal corresponding to a second region of fabric may include actuating one or more control elements, such as the one or more control elements 106 shown in and described with respect to FIGS. 1-4.

In some embodiments the method of FIG. 6 may further comprise producing the second signal based on a predicted effect of the second signal on the one or more control elements 106.

Figure 7:
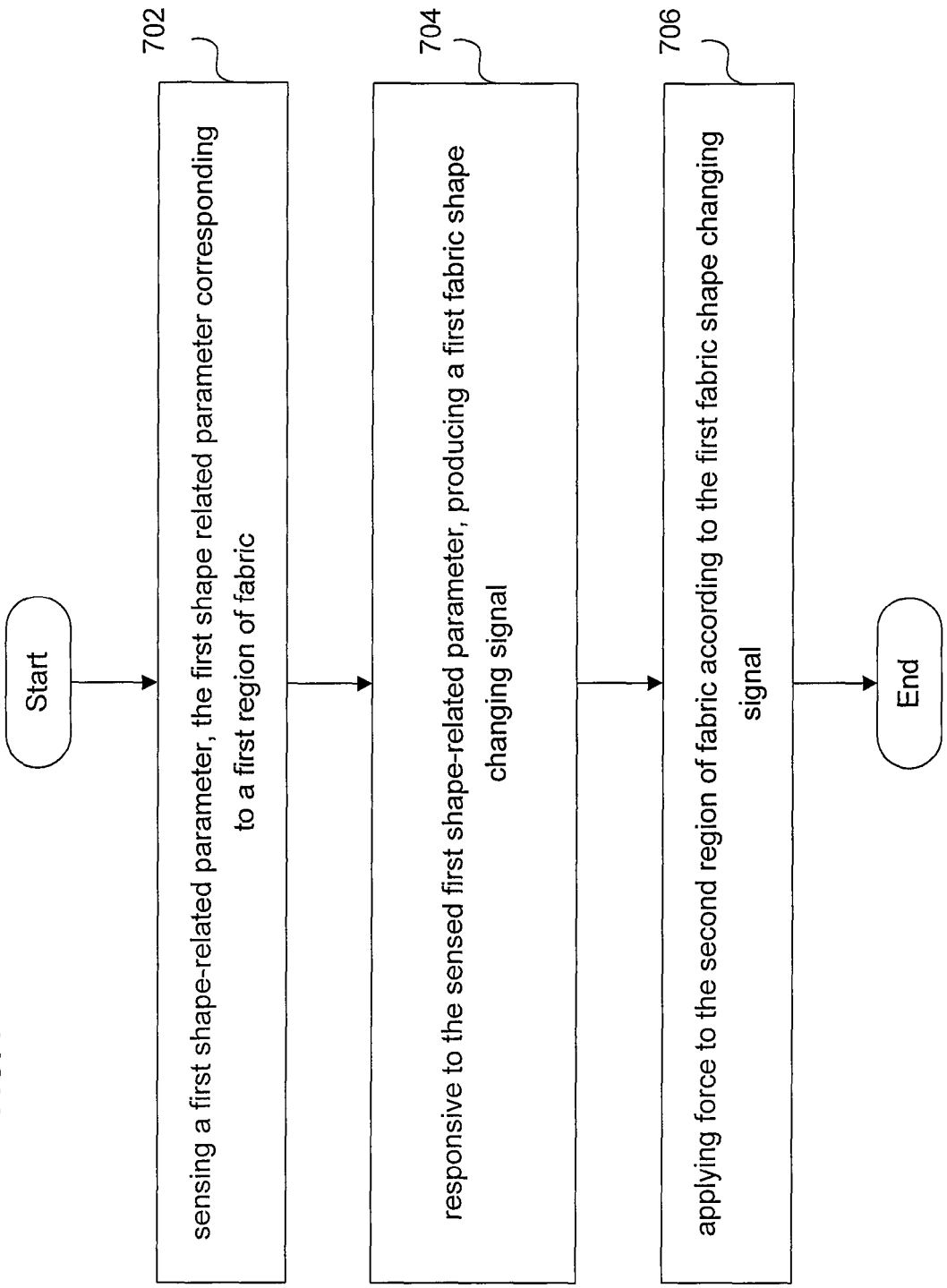
FIG. 7 shows a flow chart depicting a method.
Figure 8:
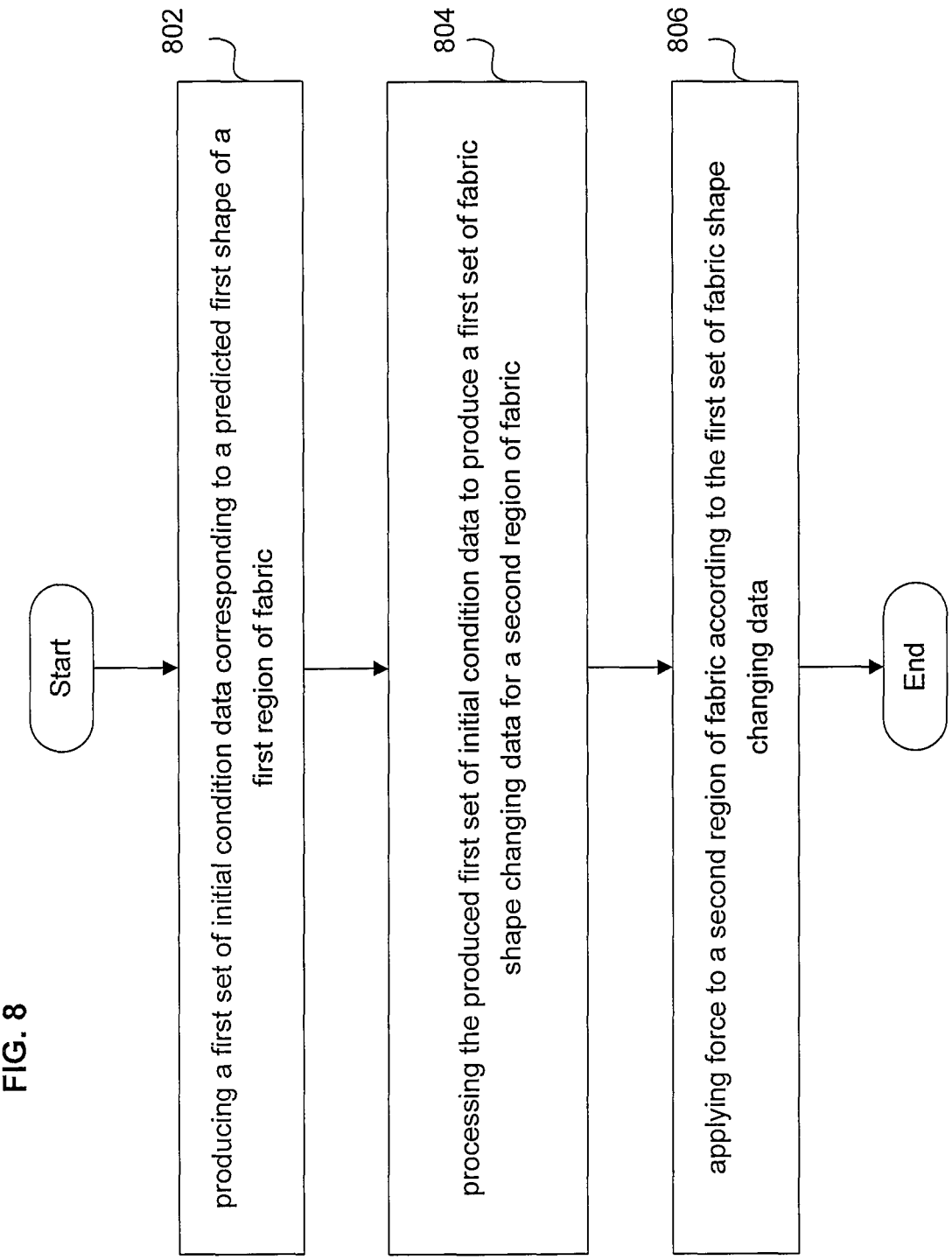
FIG. 8 shows a flow chart depicting a method.

Although the previously described methods are described with respect to the Flow Chart of FIG. 6, many of these methods apply to the methods of the Flow Charts of FIGS. 7 and 8. Further, the methods as will be described with respect to the Flow Charts of FIGS. 7 and 8 may apply to the method of FIG. 6.

In another embodiment, depicted in the Flow Chart of FIG. 7, a method comprises: (702) sensing a first shape-related parameter, the first shape related parameter corresponding to a first region of fabric; (704) responsive to the sensed first shape-related parameter, producing a first fabric shape changing signal; and (706) applying force to the second region of fabric according to the first fabric shape changing signal.

In this embodiment, the first region of fabric may correspond substantially to the second region of fabric, the first region of fabric may partially overlap the second region of fabric, and/or the first region of fabric may be entirely different from the second region of fabric.

The method corresponding to the Flow Chart of FIG. 7 may be understood with respect to FIGS. 1-5, where the first and second regions of fabric may correspond to one or more portions of a garment, such as the garment 200 shown in FIG. 2.

The method may further comprise dynamically varying the force applied to the second region of fabric according to the first fabric shape changing signal. Dynamically variable control elements 106 have been described previously with respect to FIGS. 1-5.

In one embodiment, sensing a first shape-related parameter may include measuring at least one of a voltage, a change in reflectivity, a change in electrical impedance, or a change in optical properties. In another embodiment, sensing a first shape-related parameter may include receiving at least one of an electromagnetic signal, an ultrasonic signal, an image, or a coordinate. Sensors 104 configured to measure and/or receive such parameters have been described previously.

In one embodiment, producing a first fabric shape changing signal may include processing a second signal corresponding to the sensed first shape-related parameter to produce the first fabric shape changing signal. For example, the processing may be done by the circuitry 108 and discussed with respect to FIGS. 1-5. In this embodiment, processing a second signal corresponding to the sensed first shape-related parameter to produce the first fabric shape changing signal may include using a computational model to produce the first fabric shape changing signal responsive to the second signal, which may further include simulating a response of the second region of fabric to one or more hypothetical forces. Such a hypothetical force may be an externally applied force, a force applied by the one or more control elements 106, a force applied by the wearer, or a different kind of force.

In some embodiments, applying force to the second region of fabric according to the first fabric shape changing signal may further include irreversibly changing at least a first portion of the second region of fabric. Such irreversibly changes may occur, for example, where the one or more control elements 106 are configured to, for example, irreversibly stretch or bend the fabric 102, or perform a different operation on the fabric 102 such that it is irreversibly changed.

Although the previously described methods are described with respect to the Flow Chart of FIG. 7, many of these methods apply to the methods of the Flow Charts of FIGS. 6 and 8. Further, the methods as have been/will be described with respect to the Flow Charts of FIGS. 6 and 8 may apply to the method of FIG. 7.

In another embodiment, depicted in the Flow Chart of FIG. 8, a method comprises: (802) producing a first set of initial condition data corresponding to a predicted first shape of a first region of fabric; (804) processing the produced first set of initial condition data to produce a first set of fabric shape changing data for a second region of fabric; and (806) applying force to a second region of fabric according to the first set of fabric shape changing data.

In this embodiment, producing a first set of initial condition data corresponding to a predicted shape of a first region of fabric may include receiving a signal indicative of the first shape of the first region of fabric, and predicting the first shape of the first region of fabric according to the received signal. The received signal may be, for example, the signal 204 as shown in FIG. 2, where the signal 204 is produced by the one or more sensors 104. Further, predicting the first shape of the first region of fabric according to the received signal and producing a first set of initial condition data corresponding to a predicted shape of a first region of fabric may be accomplished with the circuitry 108 as shown in FIGS. 1-5.

Although the previously described methods are described with respect to the Flow Chart of FIG. 8, many of these methods apply to the methods of the Flow Charts of FIGS. 6 and 7. Further, the methods as previously described with respect to the Flow Charts of FIGS. 6 and 7 may apply to the method of FIG. 8.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit a device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user is shown/described herein as a single illustrated figure, those skilled in the art will appreciate that user may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. An apparatus comprising:
   a garment including:
      a fabric;
         one or more sensors, the one or more sensors being arranged to detect a shape-related parameter of the fabric and responsive to the detected shape-related parameter to produce a first signal; and
         one or more control elements responsive to a second signal and arranged to provide a force on the fabric corresponding to the second signal; and
   circuitry responsive to the first signal to determine an initial shape of the fabric, to determine a change in the fabric shape according to a difference between the initial shape of the fabric and a target shape, and to produce the second signal according to the determined change in the fabric shape.

2. The apparatus of claim 1 wherein the circuitry is further responsive to stored information to determine the change in the fabric shape.

3. The apparatus of claim 2 wherein the stored information includes a previously-measured shape-related parameter.

4. The apparatus of claim 1 wherein the circuitry is further responsive to a user input to determine the change in the fabric shape.

5. The apparatus of claim 1 wherein the fabric is substantially elastic.

6. The apparatus of claim 1 wherein the one or more sensors is integral to the fabric.

7. The apparatus of claim 1 wherein the one or more control elements is integral to the fabric.

8. The apparatus of claim 1 wherein the circuitry is integral to the garment.

9. The apparatus of claim 1 wherein the circuitry is further configured to utilize a computational model to predict the change in the fabric shape.

10. In an apparatus comprising a fabric coupled to electronic circuitry, a method comprising:
sensing a shape-related parameter, the shape-related parameter corresponding to a region of the fabric;
producing data corresponding to an initial shape of the region of the fabric according to the sensed shape-related parameter;
responsive to the produced data corresponding to the initial shape, selecting a target shape of the region of fabric and producing a fabric shape changing signal, the fabric shape changing signal being selected to produce the target shape of the region of the fabric; and
applying force to the region of the fabric according to the fabric shape changing signal to produce the target shape.

11. The method of claim 10 wherein the region of the fabric forms at least a portion of a garment.

12. The method of claim 10 wherein sensing a shape-related parameter includes:
receiving at least one of an electromagnetic signal, an ultrasonic signal, an image, and a coordinate.

13. The method of claim 10 wherein applying force to the region of the fabric according to the fabric shape changing signal includes:
applying a voltage across an electroactive polymer.

14. The method of claim 10 wherein applying force to the region of the fabric according to the fabric shape changing signal includes:
actuating a mechanical metamaterial.

15. The method of claim 10 wherein applying force to the region of the fabric according to the fabric shape changing signal includes:
providing at least one of a magnetic, hydraulic, pneumatic, electrical, and a thermally induced force to the region of the fabric.

16. The method of claim 10 wherein applying force to the region of the fabric according to the fabric shape changing signal includes:
providing a force between a first sub-region of the region of the fabric and a second sub-region, different from the first sub-region, of the region of the fabric.

17. The method of claim 10 wherein applying force to the region of the fabric according to the fabric shape changing signal includes:
providing a force to at least one fiber in the region of the fabric, wherein providing a force to the at least one fiber in the region of the fabric includes applying at least one of a longitudinal stretching force, a lateral force, a bending moment, a bending force, and a torque.

18. The method of claim 10 wherein producing a fabric shape changing signal includes:
processing a second signal corresponding to the sensed shape-related parameter to produce the fabric shape changing signal.

19. The method of claim 18 wherein processing a second signal corresponding to the sensed shape-related parameter to produce the fabric shape changing signal includes:
using a computational model to produce the fabric shape changing signal responsive to the second signal.

20. The method of claim 19 wherein using a computational model to produce the fabric shape changing signal responsive to the second signal includes:
simulating a response of the region of the fabric to one or more hypothetical forces.

21. The method of claim 18 wherein processing a second signal corresponding to the sensed shape-related parameter to produce the fabric shape changing signal includes:
comparing the second signal to a reference signal.

22. The method of claim 10 wherein the shape changing signal includes at least one of electromagnetic energy, electrical energy, ultrasonic energy, and acoustic energy.

23. The method of claim 18 wherein the second signal includes at least one of electromagnetic energy, electrical energy, ultrasonic energy, and acoustic energy.

24. The method of claim 18 wherein processing a second signal corresponding to the sensed shape-related parameter to produce the fabric shape changing signal includes:
determining an initial shape of the region of the fabric.

25. The method of claim 24 wherein processing a second signal corresponding to the sensed shape-related parameter to produce the fabric shape changing signal further includes:
determining an adjusted shape of the region of fabric.

26. The method of claim 24 wherein processing a second signal corresponding to the sensed shape-related parameter to produce the fabric shape changing signal further includes:
comparing the initial shape of the region of the fabric to the target shape; and
determining the fabric shape changing signal according to a difference between the initial shape of the region of the fabric and the target shape.

27. The method of claim 10 wherein the producing the fabric shape changing signal is further responsive to a fabric property, wherein the fabric property includes at least one of fiber type, fiber dynamics, weave, mass, thickness, density, and reflective property of the fabric.

28. The method of claim 10 wherein applying force to the region of the fabric according to the fabric shape changing signal includes:
irreversibly changing at least a portion of the region of the fabric.

29. The method of claim 10 wherein the shape-related parameter includes at least one of a force, a stress, a pressure, a strain, a bend, a twist, a deformation, a geometry, a surface topology, an orientation, a reflective property, and a position of one or more portions of the garment.

30. An apparatus comprising:
one or more sensors, the one or more sensors being arranged to detect a shape-related parameter of a fabric and responsive to the detected shape-related parameter to produce a first signal;
a garment including:
the fabric; and one or more control elements arranged to provide a force on the fabric corresponding to a second signal different from the first signal; and circuitry responsive to the first signal to determine an initial shape of the fabric, to determine a change in the fabric shape according to a difference between the initial shape of the fabric and a target shape, and to produce the second signal according to a first determined change in the fabric shape.

31. The apparatus of claim 30 wherein at least one of the one or more sensors is external to the garment.

32. The apparatus of claim 30 further comprising:

a display operably connected to at least one of the one or more sensors to show information related to at least a portion of the garment.

33. The apparatus of claim 32 wherein the display is configured to show an image of at least a portion of the garment.

* * * * *